United States Patent [19]

Matson

[11] Patent Number: 4,800,227

[45] Date of Patent: Jan. 24, 1989

[54] PROCESS FOR THE PRODUCTION OF LACTAMS

[75] Inventor: Michael S. Matson, Bartlesville, Okla.

[73] Assignee: Phillips Petroleum Company, Bartlesville, Okla.

[21] Appl. No.: 642,011

[22] Filed: Aug. 20, 1984

[51] Int. Cl.$^4$ .................................. C07D 201/08
[52] U.S. Cl. ..................... 548/543; 546/216; 540/538
[58] Field of Search ............... 548/543, 552; 546/216; 540/538

[56] References Cited

U.S. PATENT DOCUMENTS

| | | | |
|---|---|---|---|
| 3,080,377 | 3/1963 | Liao | 260/326.5 |
| 3,092,638 | 6/1963 | Liao et al. | 548/552 |
| 3,198,808 | 8/1965 | Himmele et al. | 548/552 |
| 3,546,095 | 12/1970 | Kittrell | 208/60 |
| 3,681,387 | 8/1972 | Hollstein et al. | 260/326.5 FN |
| 3,781,298 | 12/1973 | Davis | 260/326.5 FN |
| 3,812,148 | 5/1974 | Hollstein et al. | 260/326.5 FN |
| 3,812,149 | 5/1974 | Hollstein | 260/326.5 FN |
| 3,884,936 | 5/1975 | Hollstein | 260/326.5 FN |
| 4,263,175 | 4/1981 | Pesa et al. | 252/473 |

*Primary Examiner*—Glennon H. Hollrah
*Assistant Examiner*—D. B. Springer
*Attorney, Agent, or Firm*—Williams, Phillips & Umphlett

[57] ABSTRACT

A one-step method for the reductive amination of a heterocyclic to produce a nitrogen-containing heterocyclic. The feedstock is contacted with a mixed metal catalyst in which the metal comprises palladium and one of ruthenium, rhodium or rhenium.

19 Claims, No Drawings

PROCESS FOR THE PRODUCTION OF LACTAMS

This invention relates to a catalytic process for the production of lactams.

BACKGROUND OF THE INVENTION

Various processes for producing lactams such as pyrrolidones from feedstocks such as maleic anhydride are known. Lactams are useful as solvents and as monomers, for example. Improved processes for producing lactams with good selectivity and yield are desired.

SUMMARY OF THE INVENTION

An object of this invention is to provide an improved process for producing lactams from a feedstock selected from dicarboxylic acid anhydrides, carboxylic diacids, imides and lactones, said feedstock having 4 to 6 carbon atoms in the backbone.

The process is carried out by contacting the feedstock with a catalyst system containing palladium and at least one second metal selected from ruthenium, rhodium or rhenium. The reaction is preferably carried out in a liquid medium optionally in the presence of at least one of aminating agent and a hydrogenating agent, depending on the feedstock. Where the feedstock is maleic or succinic anhydride, it can be hydrogenated and aminated in a one-step process in high yield and good selectivity especially with a palladium-ruthenium catalyst.

DETAILED DESCRIPTION OF THE INVENTION

Feedstocks

Imides, dicarboxylic acid anhydrides, carboxylic diacids and/or lactones can be brought together with the catalyst system of the invention. Suitable feedstocks contain 4 to 6 carbon atoms in their backbone. The feedstocks can be hydrocarbyl-substituted if desired, by substituting a hydrocarbyl group for a hydrogen attached to one of the backbone, usually ring carbon atoms. The feedstocks can be unsaturated if desired. Generally speaking, the feedstock will contain from 4 to 12 carbon atoms per molecule, usually from 4 to 6 carbon atoms per molecule.

The preferred feedstock is selected from the group consisting of maleic anhydride, maleic acid, succinic anhydride and succinic acid, most preferably maleic anhydride because it is cheap and readily available. These feedstocks are preferred because they will yield 2-pyrrolidone, a very desirable product, in good yields in a one-stage reductive amination process, as demonstrated by the examples.

Where the feedstock has been selected from anhydrides and their corresponding di-acids, and lactones, an aminating agent is preferably brought together with the feedstock and the catalyst. Ammonia or primary amines having up to about 10 carbon atoms are good aminating agents. The primary amine can contain an alkyl group having from 1 to about 4 carbon atoms or aryl groups having from 6 to about 10 carbon atoms, if desired. Methyl amine is the preferred amine. Aqueous ammonia is the preferred aminating agent for the production of unsubstituted 2-pyrrolidone from maleic or succinic anhydride or di-acid.

Hydrogenating Agent

Where the feedstock is selected from imides or anhydrides and their corresponding di-acids, a hydrogenating agent, preferably molecular hydrogen, is brought together with the feedstock and the catalyst.

Reaction Medium

The process is preferably carried out in a polar liquid which does not yield undesired products. Water is preferred due to its availability and low cost, but other polar liquid reaction mediums, particularly ethers such as tetrahydrofuran or dioxane are also suitable.

Amounts

Where the aminating agent and the hydrogenating agent are to be used, it is preferred that they be present in excess of the stoichiometric amount. Good results can be obtained by using the molar proportions of feedstock, aminating agent, catalyst and liquid reaction medium listed in Table I below, as calculated for maleic anhydride, ammonia, water and a Pd-Ru on alumina catalyst. Catalyst proportions are calculated on a basis of weight per mole of maleic anhydride.

TABLE I

| Reagents | Reactant Quantities | | |
|---|---|---|---|
| | Generally | Preferred | Most Preferred |
| Maleic Anhydride[a] | 1 | 1 | 1 |
| Ammonia[a] | 1–5 | 1.2–2 | 1.3–1.8 |
| Water[a,b] | 3–25 | 8–20 | 11–15 |
| Catalyst[c] | 0.2–15.0 | 2.0–12.0 | 5.0–8.0 |
| Catalyst metal[d] | 0.01–1.0 | 0.1–0.6 | 0.2–0.5 |

[a]Expressed as moles.
[b]Total H$_2$O, including reaction diluent and NH$_4$OH solution.
[c]Expressed as grams of catalyst (metal + support) per mole of maleic anhydride, using supported catalyst containing 5 weight percent metal.
[d]Grams of catalyst metal per mole of maleic anhydride.

Catalysts

Catalysts containing palladium and at least one of ruthenium, rhodium and rhenium can be employed for the reductive amination of feedstocks according to this invention. Preferably the active metal component of the catalyst consists essentially of a mixture of palladium and one of ruthenium, rhodium or rhenium. The preferred combination is palladium and ruthenium. The catalyst can be used in any of several forms, unsupported or supported. It can be a mixture of powders, granules or pellets of the metals or supported metals. It can be an alloy of the metals. Compounds of the metals can be mixed in solution, or in dry form, preferably placed on a suitable support, and normally reduced to the metallic form prior to use under reaction conditions. A mixture of ruthenium, rhodium or rhenium, preferably ruthenium supported on carbon or alpha-alumina and palladium supported on carbon or alpha-alumina is presently preferred. These metals are commercially available on catalyst supports such as alumina or carbon, and thus can be conveniently combined in the desired proportions.

Any suitable catalyst support material can be used which is inert and stable under reaction conditions, such as alumina, silica-alumina, silica, zirconia or carbon. Alumina and carbon are presently preferred. The support can be in various particulate forms such as powder, pellets and the like, depending upon requirements of the reactor system. The metals of the catalyst system can be present in amounts in the range of from about 0.2 to about 15 weight percent of the total catalyst, preferably about 1 to about 10 weight percent, and most preferably about 2–6 weight percent for a supported catalyst in powder form.

The proportions of the metals in the catalyst are a significant feature of the instant invention. Such proportions can be expressed as the weight or mole fraction of the non-palladium second metal to the total catalytic metal (palladium+second metal). In terms of the preferred metals palladium and ruthenium, based on the examples herein the weight fraction Ru/(Ru+Pd) will usually be in the range of from about 0.1 to about 0.9, preferably from about 0.2 to about 0.8, and most preferably from about 0.3 to about 0.7.

The examples herein demonstrate that the mixture of metals produced improved yields compared with those of the single metals over a broad range of ratios, which is surprising and unexpected. Increasing the pressure generally increases yield with a given catalyst, but preferred ruthenium weight fractions can be selected for the expected operational pressure range.

Process Conditions

In carrying out the inventive process, the feedstock and the aminating and hydrogenating agents when used are contacted with the catalyst described above, preferably in the presence of a polar liquid reaction medium, for carrying out a chemical reaction. The inventive process can be carried out using various techniques and reactors, provided the reactor inner surfaces are inert to the reactants. Stainless steeel is a preferred material for the reactor inner walls, but preferably should be low in nickel content to avoid influencing the reaction. In a controlled experiment, a reactor of Hastelloy, which contains nickel, gave a lower yield than one of stainless steel 316.

Both batch and continuous type processes are contemplated as well as recycle of the reaction product or a portion thereof to the reaction mixture and regeneration and recycle of the catalyst.

While the reaction can be carried out under a broad range of reaction conditions, to obtain best results from the catalysts described the reaction conditions are preferably maintained within preferred ranges. The reaction temperature can generally range from about 100° C. to about 400° C., preferably from about 200° C. to about 300° C., and most preferably from about 240° C. to about 270° C.

The reactant mixture should generally be maintained at the desired temperature for a period of time in the range of from about 0.1 to about 5 hours, depending upon the other process conditions. For purposes of comparison under similar conditions a reaction time of about 3 hours was found satisfactory for the batch reactions described herein. Under optimum conditions the reaction was generally complete within about 1.5 hours. However, in continuous reaction processes the reaction time can be different and will likely be shorter.

The process can be carried out at pressures in the range of from about 500 to about 5,000 psig, with higher product yields generally obtained at the higher pressures. Based upon observations of the batch reactions described herein, the pressure should preferably be maintained in the range of from about 1000 to about 4000 psig, more preferably from about 2000 to about 3000 psig, and most preferably, from about 2400 to about 3000 psig.

A stoichiometric excess of hydrogen and ammonia or primary amine should be present in the reaction mixture. The quantity of hydrogen available can be controlled by pressurizing the reactor with hydrogen. The molar ratio of ammonia or amine to the feedstock will usually range from 1:1 to about 5:1, preferably from about 1:1 to about 2:1.

The process is preferably carried out in the presence of a polar liquid reaction medium, for which water is presently preferred. When water is used, the amount present relative to the heterocyclic anhydride or corresponding acid can be significant. The molar ratio of total water (including both water added directly and with the ammonium hydroxide) to the feedstock will generally be in the range of from about 3:1 to about 25:1, usually in the range from about 8:1 to about 18:1, and preferably in the range from about 10:1 to about 17:1.

The pyrrolidones or other reaction products obtained upon completion of the reaction can be recovered by suitable known separation techniques, e.g. solvent extraction or fractional distillation.

The invention will be further illustrated by the following non-limiting examples.

EXAMPLE I

The catalysts, 5 percent ruthenium/alumina (powder) and 5 percent palladium/alumina (powder) were purchased from Strem Chemicals (Newbury, MA), Alpha Products (Danvers, MA) or Engelhard Industries (Edison, NJ) and were used as received. The catalyst portions were added to an autoclave, which had been purged with nitrogen, and the maleic anhydride, water, and ammonia were then added to the reactor also. The reactor was sealed, the nitrogen was replaced with hydrogen and the hydrogen pressure was raised to the reaction pressure desired. Stirring was begun and the reactor was heated to the desired reaction temperature. Hydrogen was consumed in the reaction as the temperature was increased and as the reaction proceeded. Hydrogen pressure was maintained substantially constant throughout the reaction by a pressure regulator.

After the desired reaction time was completed the reactor was cooled to near room temperature, the pressure was vented, the reactor was opened and the reaction mixture removed. Samples of the reaction mixture were analyzed by gas-liquid chromatography and the results were made quantitative through the use of internal standards.

The results of varying ratios of ruthenium to palladium, or ruthenium weight fraction, while keeping the total amount of catalyst constant in the reductive amination of maleic anhydride to produce 2-pyrrolidone are shown in Table II. In these reactions a 300 milliliter stainless steel reactor was used. Water (100 mL) was mixed with the maleic anhydride (MA) (50 grams) before the addition of ammonium hydroxide (46 grams).

It is seen from runs 1 and 7, 8 and 19, and 20 and 26 that palladium and ruthenium each will catalyze the reductive amination of maleic anhydride. Runs 4, 12 and 23 show that using equal amounts of these two catalysts in a mixture provides definite improvements in yields over those obtained by either catalyst alone. The optimum mixture for the formation of the pyrrolidone (butyrolactam) varied somewhat with the reaction pressure.

TABLE II

Formation of 2-Pyrrolidone Using Various Ru/Pd Ratios and Pressures

| Run | Wt. Ru (gms) | Wt. Pd (gms) | Ru (Ru + Pd)[b] | Press. (psig) | Temp. (°C.) | Yields[a], mole % % 2-PYR | % BLO | % SI | % SA |
|---|---|---|---|---|---|---|---|---|---|
| 1  | 0.00 | 3.00 | 0.00 | 1200 | 250 | 39 | — | 8.0 | — |
| 2  | 1.00 | 2.00 | 0.33 | 1200 | 250 | 64 | — | 2.1 | — |
| 3  | 1.00 | 2.00 | 0.33 | 1200 | 270 | 71 | 0.5 | 1.2 | — |
| 4  | 1.50 | 1.50 | 0.50 | 1200 | 250 | 69 | 0.5 | 1.4 | — |
| 5  | 1.50 | 1.50 | 0.50 | 1200 | 270 | 68 | 0.6 | 0.7 | — |
| 6  | 2.00 | 1.00 | 0.67 | 1200 | 250 | 67 | 0.6 | 1.6 | 6.0 |
| 7  | 3.00 | 0.00 | 1.00 | 1200 | 250 | 59 | 0.5 | 1.6 | 7.6 |
| 8  | 0.00 | 3.00 | 0.00 | 1700 | 250 | 55 | — | 1.0 | — |
| 9  | 0.60 | 2.40 | 0.20 | 1700 | 250 | 68 | 0.5 | 0.6 | — |
| 10 | 1.20 | 1.80 | 0.40 | 1700 | 250 | 81 | — | 1.1 | — |
| 11 | 1.35 | 1.65 | 0.45 | 1700 | 250 | 74 | — | — | — |
| 12 | 1.50 | 1.50 | 0.50 | 1700 | 250 | 78 | — | — | — |
| 13 | 1.50 | 1.50 | 0.50 | 1700 | 250 | 75 | — | — | — |
| 14 | 1.80 | 1.20 | 0.60 | 1700 | 250 | 81 | — | — | — |
| 15 | 2.00 | 1.00 | 0.67 | 1700 | 250 | 84 | — | — | — |
| 16 | 2.25 | 0.75 | 0.75 | 1700 | 250 | 79 | — | 1.0 | — |
| 17 | 2.50 | 0.50 | 0.83 | 1700 | 250 | 83 | — | — | — |
| 18 | 2.70 | 0.30 | 0.90 | 1700 | 250 | 82 | 0.5 | 0.5 | — |
| 19 | 3.00 | 0.00 | 1.00 | 1700 | 250 | 59 | 1.0 | 2.0 | — |
| 20 | 0.00 | 3.00 | 0.00 | 2400 | 250 | 53 | — | 3.5 | 11.6 |
| 21 | 0.75 | 2.25 | 0.25 | 2400 | 250 | 76 | — | — | — |
| 22 | 1.05 | 1.95 | 0.35 | 2400 | 250 | 86 | — | — | — |
| 23 | 1.50 | 1.50 | 0.50 | 2400 | 250 | 88 | — | — | — |
| 24 | 2.05 | 0.95 | 0.68 | 2400 | 250 | 82 | 1.0 | 1.0 | — |
| 25 | 2.50 | 0.50 | 0.83 | 2400 | 250 | 83 | — | — | — |
| 26 | 3.00 | 0.00 | 1.00 | 2400 | 250 | 72 | — | 1.0 | — |

[a]2-PYR = 2-Pyrrolidone
BLO = γ-butyrolactone
SI = succinimide
SA = succinic anhydride
— = product not detected in the analysis
[b]Ruthenium weight fraction

EXAMPLE II

Under reaction conditions that were otherwise the same as shown in Example I, the effects of changing pressure are shown in a series of runs listed in Table III.

TABLE III

Effect of Pressure on the Reductive Amination of Maleic Anhydride

| Run | Ru[b] (Ru + Pd) | Press. (psig) | Temp. (°C.) | Yields[a] mole % % 2-PYR | % BLO | % Si | % SA |
|---|---|---|---|---|---|---|---|
| 6  | 0.67 | 1200 | 250 | 67 | 0.3 | 0.8 | — |
| 15 | 0.67 | 1700 | 250 | 84 | — | — | — |
| 27 | 0.67 | 2000 | 250 | 89 | — | — | — |
| 28 | 0.67 | 2400 | 250 | 83 | — | — | — |
| 4  | 0.50 | 1200 | 250 | 69 | 0.5 | 1.4 | — |
| 13 | 0.50 | 1700 | 250 | 76 | — | — | — |
| 23 | 0.50 | 2400 | 250 | 88 | — | — | — |

[a]2-PYR = 2-pyrrolidone
BLO = γ-butyrolactone
SI = succinimide
SA = succinic anhydride
[b]Ruthenium weight fraction It is seen that as the pressure is increased the yield of the butyrolactone is increased to a maximum at about 2000 lbs pressure when the ruthenium weight fraction is approximately 0.67. When that weight fraction is 0.5, however, no maximum is apparent up to 2400 lbs pressure.

EXAMPLE III

The effects of varying the temperature through several runs in which the pressure was held at 2400 psig in each case, but conditions were otherwise the same as shown in Example I, are demonstrated in Table IV.

TABLE IV

Effect of Temperature on the Reductive Amination of Maleic Anhydride

| Run | Ru (Ru + Pd) | Press. (psig) | Temp. (°C.) | Yield, 2-Pyrrolidone, mole % |
|---|---|---|---|---|
| 21 | 0.50 | 2400 | 240 | 78 |
| 23 | 0.50 | 2400 | 250 | 88 |
| 29 | 0.50 | 2400 | 260 | 86 |
| 30 | 0.50 | 2400 | 270 | 80 |

It is seen that the temperature does play an important role in determining the final yield of 2-pyrrolidone and under the present conditions a maximum yield was reached at about 250° C.

Although only a few embodiments of the present invention have been specifically described above, it should be appreciated that many additions and modifications can be made without departing from the spirit and scope of the invention. These and all other modifications are intended to be included within the scope of the present invention, which is to be limited only by the following claims:

I claim:

1. A process for producing a lactam comprising contacting a feedstock selected from the group consisting of acid anhydrides, dicarboxylic acids, lactones, and imides, said feedstock having 4 to 6 carbon atoms in the backbone with a catalyst system comprising palladium and at least one second metal selected from the group consisting of ruthenium, rhodium and rhenium under conditions to convert at least a portion of the feedstock to the lactam.

2. A process for producing a lactam comprising contacting a feedstock selected from the group consisting of acid anhydrides, dicarboxylic acids, lactones, and imides, said feedstock having 4 to 6 carbon atoms in the backbone, hydrogen, and an aminating agent, with a catalyst system comprising palladium and at least one second metal selected from the group consisting of ruthenium, rhodium and rhenium in a polar liquid medium under conditions to convert at least a portion of the feedstock to the lactam.

3. A process as in claim 2 wherein the feedstock is selected from acid anhydrides and their corresponding acids.

4. A process in accordance with claim 2 wherein said second metal of said catalyst consists essentially of ruthenium.

5. A process in accordance with claim 2 wherein said catalyst further comprises a particulate support selected from the group consisting of alumina, silica-alumina, silica, zirconia and carbon and in which the palladium and the ruthenium are deposited on the particulate support.

6. A process in accordance with claim 5 wherein said catalyst consists essentially of ruthenium and palladium on a particulate alumina support.

7. A process in accordance with claim 6 where the ruthenium weight fraction of the catalyst, defined as wt. Ru/wt. (Ru+Pd), is in the range of from about 0.1 to 0.9.

8. A process in accordance with claim 6 wherein said ruthenium weight fraction is in the range of from about 0.3 to about 0.8.

9. A process in accordance with claim 6 wherein said ruthenium weight fraction is in the range of from about 0.4 to about 0.7.

10. A process in accordance with claim 9 wherein the feedstock is selected from the group consisting of maleic anhydride, maleic acid, succinic anhydride or succinic acid.

11. A process in accordance with claim 10 wherein said aminating agent comprises ammonia.

12. A process in accordance with claim 11 wherein said polar liquid medium is selected from the group consisting of water and ethers.

13. A process in accordance with claim 12 wherein said polar liquid medium is predominantly water.

14. A process in accordance with claim 13 wherein each mole of feedstock is brought together with from about 1 to about 5 moles of ammonia and 3 to about 25 moles of water, and with about 0.01 to about 0.75 grams of mixed palladium and ruthenium contained in said catalyst.

15. A process in accordance with claim 14 wherein the feedstock comprises maleic anhydride or maleic acid and each mole of feedstock is brought together with from about 1.2 to about 2 moles of ammonia and about 12 to about 15 moles of water, and with about 0.2 to about 0.6 grams of mixed palladium and ruthenium contained in said catalyst.

16. A process in accordance with claim 15 further comprising maintaining the temperature in the range of from about 200° to about 300° C.

17. A process in accordance with claim 16 further comprising maintaining the temperature in the range of from about 240° to about 270° C.

18. A method in accordance with claim 16 further comprising maintaining the pressure in the range from about 500 to about 5000 psig by hydrogen addition.

19. A method in accordance with claim 17 further comprising maintaining the pressure in the range of from about 1500 to about 4000 psig by hydrogen addition.

* * * * *